United States Patent [19]

Scardigno et al.

[11] 4,052,452

[45] Oct. 4, 1977

[54] PROCESS FOR PREPARING GLYCOLIC ACID AND ITS POLYMERS

[75] Inventors: Salvatore Scardigno, Cesano Boscone (Milan); Luigi Rivolta, Monza (Milan); Giuseppe Caprara, Milan; Luigi Cassar, Novara, all of Italy

[73] Assignee: Montedison S.p.A., Milan, Italy

[21] Appl. No.: 600,044

[22] Filed: July 29, 1975

[30] Foreign Application Priority Data

Aug. 1, 1974 Italy .................................. 25846/74

[51] Int. Cl.$^2$ ............................................ C07C 59/06
[52] U.S. Cl. ................................................ 260/535 R
[58] Field of Search ..................................... 260/535 R

[56] References Cited

U.S. PATENT DOCUMENTS

| 2,152,852 | 4/1939 | Loder ................................ 260/535 R |
| 2,443,482 | 6/1948 | Shattuck ............................ 260/535 |
| 3,754,028 | 8/1973 | Lapporte et al. ................... 260/535 |

Primary Examiner—Paul J. Killos
Attorney, Agent, or Firm—Stevens, Davis, Miller & Mosher

[57] ABSTRACT

A process is disclosed for preparing glycolic acid and its polymers starting from formaldehyde, wherein the formaldehyde is reacted with carbon monoxide in concentrated $H_2SO_4$ as reaction medium, in the presence of a catalyst based on a compound of Cu (I) or of Ag, and at a temperature ranging from 0° to 90° C and at a pressure between 0.1 and 30 atmospheres.

6 Claims, No Drawings

PROCESS FOR PREPARING GLYCOLIC ACID AND ITS POLYMERS

This invention relates to a process for preparing glycolic acids. More particularly, it relates to a process for preparing glycolic acid and its polymers, starting from formaldehyde.

Glycolic acid is an interesting intermediate for the synthesis of ethylene glycol. Furthermore, it is useful in the descaling and cleaning of metal surfaces owing to its complexing power with respect to the ions of many heavy metals. It is also employed in some formulations of synthetic detergents, as well as in the dyeing of wool and nylon.

It is already known to obtain glycolic acid from formaldehyde by carbonylation in the presence of acid catalysts at high temperatures (200° to 300° C) and high CO pressures (about 700 atmospheres).

It has now been found in accordance with the present invention that it is possible to obtain high glycolic acid yields by effecting the carbonylation of formaldehyde under less severe temperature and pressure conditions, employing a particular reaction medium and particular catalysts.

It is the object of this invention to provide a process for preparing glycolic acid and it polymers from formaldehyde, which consists essentially in reacting formaldehyde with carbon monoxide in concentrated $H_2SO_4$ as reaction medium, in the presence of a catalyst based on a compound of Cu (I) or of Ag, and at a temperature ranging from a low as 0° to as high as 70° or 80° C or even as high as 90° C, and at a pressure between 0.1 and 30 atmospheres.

At the end of the reaction, besides glycolic acid, its polymers can be obtained.

The formaldehyde reactant may be employed either in a concentrated aqueous solution, or in the form of a cyclic or linear polymer of formaldehyde (e.g., trioxane, polyoxymethylene).

The catalysts utilized in the process according to this invention are prepared by causing a system made up of sulphuric acid and a Cu (I) or Ag compound to absorb CO.

Amongst suitable Cu (monovalent) compounds, cuprous oxide is preferred. The preferred Ag compounds are silver sulphate, silver acetate and silver carbonate.

Instead of the Cu (I) compounds per se, it is possible also to employ Cu (II) compounds associated with an equivalent amount of metallic Cu; for example, copper in powder form associated with CuO.

The sulphuric acid concentration in the reaction mass is between 50 and 100%. The molar ratio of the formaldehyde feed to the $H_2SO_4$ feed may be 1:1.

The metal+/sulphuric acid molar ratio is not critical and may vary over a very wide range; for example, from 0.001 to 0.1.

The process according to this invention is carried out at a temperature of from 0° to 90° C, the preferred range in the case of catalysts based on Cu being 20° to 60° C, and in the case of catalysts based on Ag being 20° to 80° C.

The pressure employed in carrying out the process is not a critical parameter. It is generally relatively low, between 0.1 and 30 atmospheres.

According to the present invention carbon monoxide is absorbed, under stirring, in a system consisting of concentrated sulphuric and a monovalent copper or silver compound. Formaldehyde is subsequently introduced in the form of either a concentrated aqueous solution or a cyclic or linear polymer thereof, along with CO. The amount of carbon monoxide corresponds substantially to the stoichiometric amount necessary to form the desired glycolic acid.

At the conclusion of the reaction, the mass is diluted with water. The polymeric product, if any, having the highest molecular weight is recovered by filtration.

After removal of the sulphate ion, glycolic acid is recovered along with its polymers having the lowest molecular weight by evaporation from the aqueous solutions.

The process according to the present invention offers several important advantages. The main advantage is that the reaction may be conducted under unusually mild reaction conditions, thus resulting in a reduction of costs, minimization of corrosion problems, etc.

The following non-limiting examples are given in order still better to illustrate the present invention:

EXAMPLE 1

111 ml of $H_2SO_4$ (96% by weight) were introduced into a 500 cc flask made of Pyrex glass and equipped with thermometer, stirrer, burette for gas and feed tubes. The air was replaced by CO and the mass was thermoregulated at 30° C. Subsequently, 2.86 g of $Cu_2O$ (0.02 moles) were added.

Under intense stirring, CO was gradually fed from the burette, at room pressure, as the absorption went on. 1070 Nml of CO were absorbed in 35 minutes. 40 ml of a formaldehyde aqueous solution at 38% (weight/vol.) were fed at a flow rate of 12ml/hr. At the conclusion of the formaldehyde feeding, CO absorption was allowed to continue; it stopped after about 13 hours (10,850 Nml were absorbed). The reaction mass was then poured into 500 cc of water and ice, and the insoluble part (consisting of polymers higher than glycolic acid) was filtered.

After percipitation of sulphuric acid as the barium salt and removal of the cations present in the solution by percolation over Dowex 50W resin, glycolic acid was recovered along with its lowest polymers by evaporation of water.

32.8 g of glycolic acid (calculated as the monomer) were obtained overall, the yield being 85.4% calculated on the formaldehyde introduced.

EXAMPLE 2

Operation was as in Example 1, but instead of cuprous oxide, 1.6 g of cupric oxide (0.02 moles) and 1.3 g of copper in powder form (0.0205 g atoms) were used, thus obtaining Cu carbonyl by absorption of 1000 Nml of CO in 90 minutes, successively. 11.9 g of trioxane (0.396 moles calculated as formaldehyde) dissolved in 12 ml of glacial acetic acid were fed in 2 hours under stirring at 30° C. The CO absorption continued for another hour. During the trioxane carbonylation step, 8200 Nml of CO were absorbed.

The reaction mass was poured into 500 cc of $H_2O$ and ice.

By proceeding in the same way as in Example 1, 27 g of glycolic acid calculated as monomer (yield = 89.7%) were recovered.

EXAMPLE 3

Cu carbonyl was prepared according to the procedure of Example 1. Then 23.8 g of polyoxymethylene (formaldehyde titre = 95%; 0.754 moles, calculated as formaldehyde) were fed in 100 minutes. CO absorption continued, on the whole, 12 hours; during this step 15,600 Nml of CO were absorbed.

By proceeding as in Example 1, 50.5 g of glycolic acid and its polymers were recovered, the yield being equal to 88% of glycolic acid calculated as monomer.

The glycolic acid polymers having the highest molecular weight made up about 12% of the recovered product.

EXAMPLE 4

Operation initially was illustrated in Example 1, with the exception that the temperature was 35° C and that, instead of cuprous oxide, 6.24 g of $Ag_2SO_4$ (0.02 moles) were used. 125 Nml of CO were thus absorbed in 5 minutes.

50 g of trioxane (1.67 moles calculated as formaldehyde) were then fed in 7 hours. During this time period 21,600 Nml of CO were absorbed. The temperature was then raised to 45° C and kept there for 6 hours. A further 4,820 Nml of CO were absorbed.

Finally, the temperature was brought up to 55° C and kept there for the last 8-hour reaction period. A further 3,360 Nml of CO were absorbed.

The reaction mass was poured into 500 cc of water and ice, and a solid product was separated by centrifugation.

The remaining solution, after treatment with HCl to cause the precipitation of the $Ag^+$ ion, and with $Ba(OH)_2$, to cause the precipitation of sulphuric acid as $BaSO_4$, was percolated over a Dowex 50W resin column and evaporated. 73.5 g of glycolic acid (calculated as monomer) were thus recovered.

The centrifuged solid was suspended in $H_2O$ and also treated with HCl (70% of the total Ag was thus recovered) and $Ba(OH)_2$. The resulting solution, finally, was evaporated to dryness, 23 g of glycolic acid (calculated as monomer) being thus obtained. 96.5 g of glycolic acid were obtained on the whole. The yield was 76% (calculated on the trioxane employed).

EXAMPLE 5

The following test was performed using equipment suited to carry out an improved mass transfer, with respect to the preceding tests, with a view to attaining a better kinetics.

To a solution of 25 g of $Ag_2SO_4$ in 165 ml of 96% $H_2SO_4$, after absorption of 180 Nml of CO at 50° C, 30 g of polyoxymethylene (formaldehyde content = 85%, 0.95 moles, calculated as formaldehyde) were admixed batchwise.

21,100 Nml of CO were absorbed in about 4 hours at 50° C; at the conclusion of the reaction the mass was poured into 500 cc of water and ice; the solid product was separated by centrifugation. Glycolic acid and its polymers were recovered by removing most of the sulphuric ion as sodium sulphate decahydrate and the remaining amounts as barium sulphate.

The recovered glycolic acid amounted to 61 g calculated as monomer, corresponding to a yield of 84.5% calculated on the fed polyoxymethylene.

EXAMPLE 6

200 ml of $H_2SO_4$ at 96% by weight, 0.62 g of $Ag_2SO_4$ and 20 atm. of CO were fed to a Hastelloy autoclave having a capacity of 500 cc, equipped with stirrer and thermal regulating system. After stirring for 30 minutes at 80° C, a fresh prepared solution of 30 g of polyoxymethylene (formaldehyde titre = 95% − 0.95 moles calculated as formaldehyde) in 150 ml of $H_2SO_4$ at 96% by weight was introduced into said autoclave.

A strong absorption of CO immediately occurred, which ended in about 4 minutes, the consumption CO being of 20,000 Nml.

The product was separated from the reaction mass according to the modalities described in example 1. 66.5 g of glycolic acid (calculated as monomer), corresponding to a yield of 92.0%, 92.0% were obtained in the aggregate.

What is claimed is:

1. A process for preparing glycolic acid and its polymers starting from formaldehyde, wherein the formaldehyde is reacted with carbon monoxide in concentrated $H_2SO_4$ as reaction medium, in the presence of a catalyst consisting essentially of Cu (I) or Ag oxides and acid salts thereof, and at a temperature ranging from 0° to 90° C and at a pressure between 0.1 and 30 atmospheres.

2. A process according to claim 1, wherein the formaldehyde is introduced in the form of a concentrated aqueous solution.

3. A process according to claim 1, wherein the formaldehyde is introduced in the form of a cyclic or linear polymer of formaldehyde.

4. A process according to claim 1, wherein the concentration of $H_2SO_4$ in the reaction medium ranges from 50 to 100%.

5. A process according to claim 1, wherein the catalyst is based on Cu (I) and the reaction temperature range is 20° to 60° C.

6. A process according to claim 1, wherein the catalyst is based on Ag and the reaction temperature range is 20° to 80° C.

* * * * *